(12) United States Patent
Le et al.

(10) Patent No.: US 11,701,123 B2
(45) Date of Patent: Jul. 18, 2023

(54) MECHANICAL DETACHMENT SYSTEM FOR TRANSCATHETER DEVICES

(71) Applicant: SHAPE MEMORY MEDICAL, INC., Santa Clara, CA (US)

(72) Inventors: Le Le, San Jose, CA (US); Rose Y. Leo, Livermore, CA (US); Chung Yeh, San Mateo, CA (US); Kasey Kwong, Porland, OR (US); Rochelle Marlangaue, Fremont, CA (US); Todd L. Landsman, Ojai, CA (US); Michael Barrett, Campbell, CA (US)

(73) Assignee: SHAPE MEMORY MEDICAL, INC., Santa Clara, CA (US)

( * ) Notice: Subject to any disclaimer, the term of this patent is extended or adjusted under 35 U.S.C. 154(b) by 47 days.

(21) Appl. No.: 17/407,271

(22) Filed: Aug. 20, 2021

(65) Prior Publication Data

US 2022/0054140 A1 Feb. 24, 2022

Related U.S. Application Data

(60) Provisional application No. 63/068,533, filed on Aug. 21, 2020.

(51) Int. Cl.
*A61B 17/12* (2006.01)
*A61B 90/00* (2016.01)
*A61B 17/00* (2006.01)

(52) U.S. Cl.
CPC .... *A61B 17/12113* (2013.01); *A61B 17/1214* (2013.01); *A61B 17/1219* (2013.01); *A61B 90/39* (2016.02); *A61B 2017/00867* (2013.01); *A61B 2017/12054* (2013.01); *A61B 2090/3966* (2016.02)

(58) Field of Classification Search
CPC ........ A61B 17/12109; A61B 17/12113; A61B 17/1214; A61B 17/1219; A61B 2017/00867; A61B 2017/00871; A61B 2017/12054; A61B 2017/12077; A61B 90/39; A61B 2090/3966
See application file for complete search history.

(56) References Cited

U.S. PATENT DOCUMENTS

| | | |
|---|---|---|
| 5,217,484 A | 6/1993 | Marks |
| 5,261,916 A | 11/1993 | Engelson |
| 5,350,397 A | 9/1994 | Palermo et al. |
| 5,895,391 A | 4/1999 | Farnholtz |
| 5,925,059 A | 7/1999 | Palermo et al. |
| 6,019,757 A | 2/2000 | Scheldrup |
| RE37,117 E | 3/2001 | Palermo |

(Continued)

FOREIGN PATENT DOCUMENTS

| | | |
|---|---|---|
| WO | 2002013705 A1 | 2/2002 |
| WO | 2020014536 A1 | 1/2020 |

OTHER PUBLICATIONS

Coley et al. "Endovascular occlusion with a new mechanical detachablecoil", AJR Am J Roentgenol, Oct. 1998; 171(4), pp. 1075-1079.

(Continued)

*Primary Examiner* — George J Ulsh
(74) *Attorney, Agent, or Firm* — Trop, Pruner & Hu, P.C.

(57) ABSTRACT

Embodiments include, for example, mechanical release systems for implantable medical devices.

25 Claims, 10 Drawing Sheets

(56) References Cited

U.S. PATENT DOCUMENTS

| | | |
|---|---|---|
| 6,835,185 B2 | 12/2004 | Ramzipoor et al. |
| 6,849,081 B2 | 2/2005 | Sepetka et al. |
| 6,936,058 B2 | 8/2005 | Forde et al. |
| 7,147,618 B2 | 12/2006 | Kurz |
| 7,316,708 B2 | 1/2008 | Gordon et al. |
| 7,344,558 B2 | 3/2008 | Lorenzo et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,691,124 B2 | 4/2010 | Balgobin |
| 7,708,754 B2 | 5/2010 | Balgobin et al. |
| 7,708,755 B2 | 5/2010 | Davis, III et al. |
| 7,722,636 B2 | 5/2010 | Farnan |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,942,894 B2 | 5/2011 | West |
| 7,985,238 B2 | 7/2011 | Balgobin et al. |
| 8,328,860 B2 | 12/2012 | Strauss et al. |
| 8,333,796 B2 | 12/2012 | Tompkins et al. |
| 8,377,044 B2 | 2/2013 | Coe et al. |
| 8,500,773 B2 | 8/2013 | Nardone et al. |
| 8,777,979 B2 | 7/2014 | Shrivastava et al. |
| 8,795,321 B2 | 8/2014 | Srauss et al. |
| 8,801,747 B2 | 8/2014 | Strauss et al. |
| 8,845,676 B2 | 9/2014 | Monstadt et al. |
| 8,864,789 B2 | 10/2014 | Balgobin et al. |
| 8,911,487 B2 | 12/2014 | Bennett et al. |
| 8,956,381 B2 | 2/2015 | Que et al. |
| 9,149,278 B2 | 10/2015 | Slazas et al. |
| 9,186,151 B2 | 11/2015 | Tompkins et al. |
| 9,289,215 B2 | 3/2016 | Strauss et al. |
| 9,307,996 B2 | 4/2016 | Johnson et al. |
| 9,307,999 B2 | 4/2016 | Li et al. |
| 9,375,333 B1 | 6/2016 | Aboytes et al. |
| 9,486,223 B2 | 11/2016 | Que et al. |
| 9,554,805 B2 | 1/2017 | Tompkins et al. |
| 9,579,104 B2 | 2/2017 | Beckham et al. |
| 9,615,951 B2 | 4/2017 | Bennett et al. |
| 9,622,754 B2 | 4/2017 | Ramzipoor et al. |
| 9,662,120 B2 | 5/2017 | Lagodzki et al. |
| 9,687,246 B2 | 6/2017 | Torp |
| 9,700,322 B2 | 7/2017 | Dias et al. |
| 9,775,621 B2 | 10/2017 | Tompkins et al. |
| 9,814,465 B2 | 11/2017 | Win et al. |
| 9,907,555 B2 | 3/2018 | Buiser et al. |
| 9,918,718 B2 | 3/2018 | Lorenzo |
| 9,943,313 B2 | 4/2018 | Jones et al. |
| 9,968,360 B2 | 5/2018 | Stoppenhagen et al. |
| 9,980,731 B2 | 5/2018 | Lorenzo |
| 10,299,755 B2 | 5/2019 | Tieu |
| 10,299,947 B2 | 5/2019 | Bennett et al. |
| 10,335,155 B2 | 7/2019 | Beckham et al. |
| 10,405,868 B2 | 9/2019 | Tompkins et al. |
| 10,420,563 B2 | 9/2019 | Hebert et al. |
| 10,548,605 B2 | 2/2020 | Anderson et al. |
| 10,631,869 B2 | 4/2020 | Tassoni et al. |
| 10,743,882 B2 | 8/2020 | Kleshinski et al. |
| 10,806,461 B2 | 10/2020 | Lorenzo |
| 11,051,825 B2 * | 7/2021 | Gorochow ....... A61B 17/12172 |
| 2006/0025802 A1 | 2/2006 | Sowers |
| 2006/0116714 A1 | 6/2006 | Sepetka et al. |
| 2007/0123927 A1 | 5/2007 | Farnan |
| 2008/0221654 A1 | 9/2008 | Buiser et al. |
| 2009/0036877 A1 | 2/2009 | Nardone et al. |
| 2009/0099592 A1 | 4/2009 | Buiser et al. |
| 2009/0138036 A1 | 5/2009 | Nardone et al. |
| 2010/0121350 A1 | 5/2010 | Mirigian |
| 2011/0046657 A1 | 2/2011 | Guo et al. |
| 2016/0157869 A1 | 6/2016 | Elgård et al. |
| 2016/0310703 A1 * | 10/2016 | Drake ............... A61M 25/0147 |
| 2019/0015108 A1 | 1/2019 | Maitland et al. |
| 2019/0231566 A1 | 8/2019 | Tassoni et al. |
| 2020/0146689 A1 | 5/2020 | Shabaz et al. |
| 2020/0187951 A1 | 6/2020 | Blumenstyk |
| 2020/0222057 A1 * | 7/2020 | Tassoni ............ A61B 17/12145 |
| 2020/0229957 A1 | 7/2020 | Bardsley et al. |
| 2020/0337709 A1 | 10/2020 | Kleshinski et al. |
| 2021/0085498 A1 | 3/2021 | Nygaard et al. |
| 2021/0196281 A1 * | 7/2021 | Blumenstyk ..... A61B 17/12022 |

OTHER PUBLICATIONS

Ahn et al., "Rescuemechanical thrombectomy using a retrievable stent for thromboembolicocclusion occurring during coil embolization of ruptured intracranial aneurysms", J Neurointerv Surg., Mar. 2017; 9(3), pp. 244-249.

Greben et al., "Pulmonaryarteriovenous malformation embolization: how we do it", Tech Vasc Interv Radiol., Mar. 2013, 16(1), pp. 39-44.

Marks et al., "A mechanicallydetachable coil for the treatment of aneurysms and occlusion of blood vessels", AJNR Am J Neuroradiol., May 1994, 15(5), pp. 821-827.

International Search Authority, International Search Report and Written Opinion dated Dec. 8, 2021 in International Application No. PCT/US2021/046812 (10 pages).

* cited by examiner

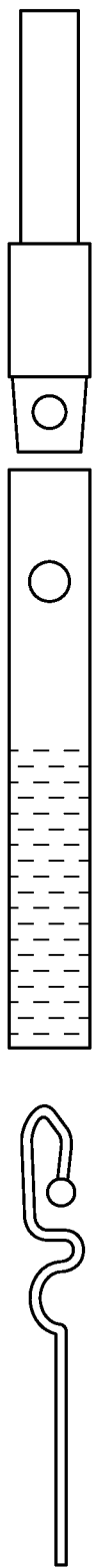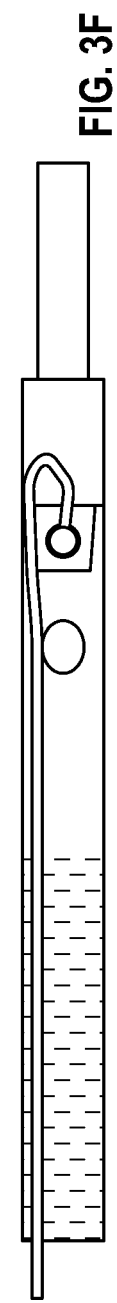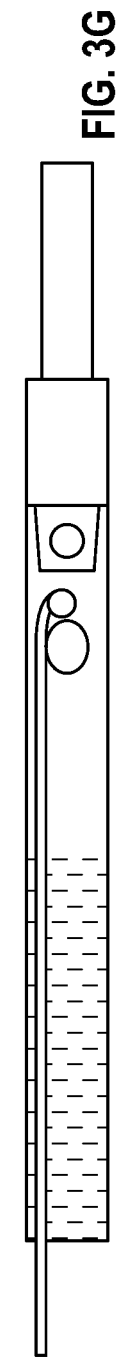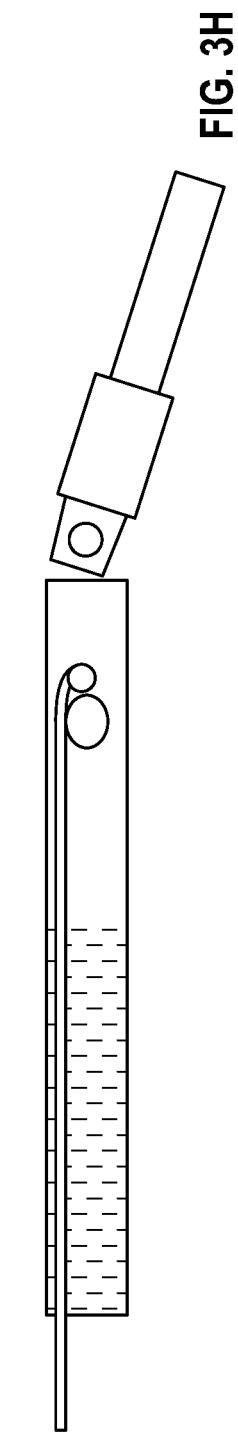
FIG. 3A FIG. 3B FIG. 3C FIG. 3D FIG. 3E FIG. 3F FIG. 3G FIG. 3H

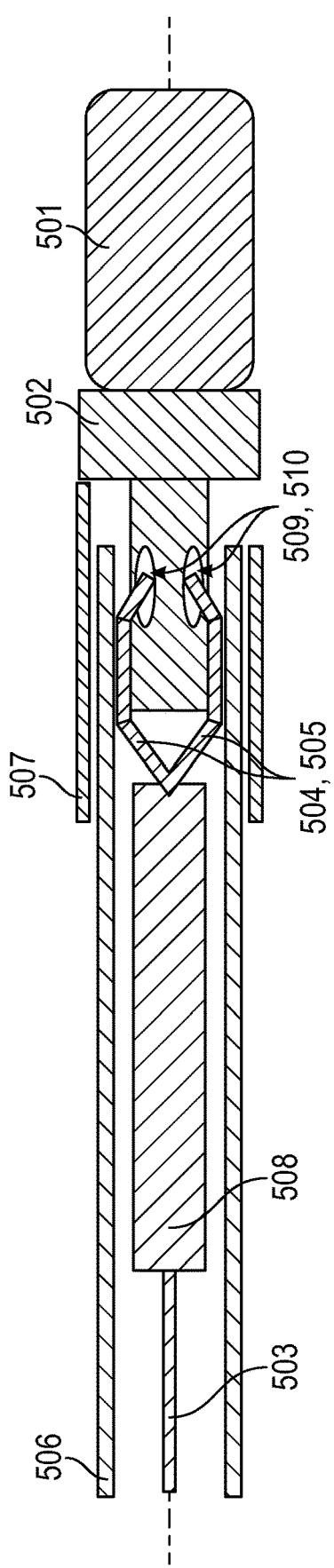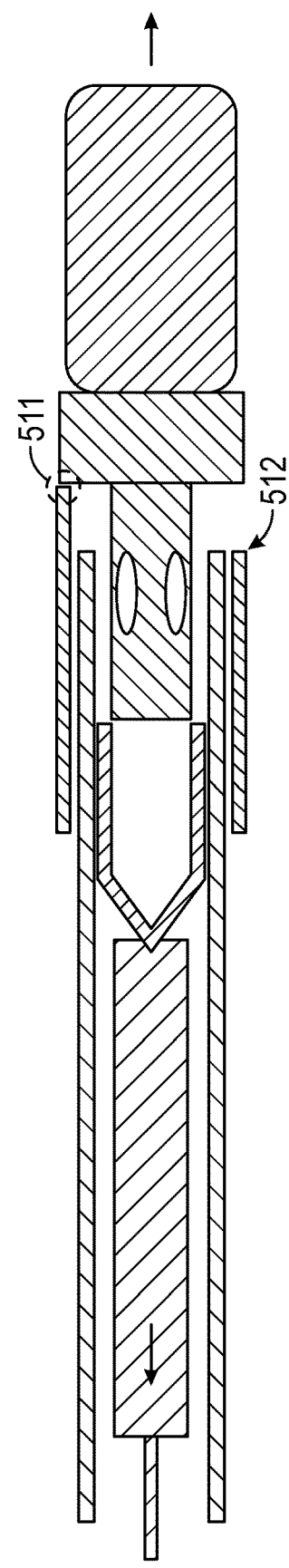
FIG. 4A
FIG. 4B

MECHANICAL DETACHMENT SYSTEM FOR TRANSCATHETER DEVICES

CROSS-REFERENCE TO RELATED APPLICATION

This application claims priority to U.S. Provisional Patent Application No. 63/068,533 filed on Aug. 21, 2020 and entitled "Mechanical Detachment System for Transcatheter Devices", the content of which is hereby incorporated by reference.

TECHNICAL FIELD

Embodiments of the invention are in the field of medical devices and, in particular, transcatheter devices.

BACKGROUND

An estimated 6 million people in the United States suffer from severe symptoms of chronic venous insufficiency. Symptoms range from dramatic skin changes to painful recalcitrant ulcers that are often found in the lower extremities. Chronic venous insufficiency is caused by weakened venous valves that can no longer prevent backflow in peripheral veins that carry blood to the heart resulting in a sudden rise in venous pressure. This hypertension can lead to the formation of varicose veins as well as venous ulcers. The greater saphenous vein is the most common region treated for chronic venous insufficiency. Previous methods of treatment of the manifestations of chronic venous insufficiency include manual compression, surgical ligation and stripping, sclerotherapy, and endovenous ablation of the greater saphenous vein. Endovenous ablation has many downfalls. With endovenous ablation the patient experiences pain, either from the anesthetic injections or from the laser treatment. Further, recanalization may occur as the physician must uniformly ablate the whole cross-section of the vein and control the laser's pull-back speed. Many other complications may result such as deep vein thrombosis, bruising, dysesthesia, skin burns, bruising, thrombophlebitis, and nerve damage.

United States Patent Application 20190015108 describes an embodiment that uses polyurethane shape memory polymer (SMP) foam to selectively occlude regions of vasculature where persistent blood flow may cause complications. The morphology and chemistry of the foam allows it to be compressed and loaded into an introducer and advanced through a catheter to the target region. Upon contact with circulating blood, the foam expands (e.g., within 2, 4, 6, 8, or 10 minutes after contacting blood) to its original geometry and completely fills the vessel lumen. The procedure utilizes minimally invasive techniques.

United States Patent Application 20190015108 further provides that embodiments may utilize a number of delivery mechanisms. One such mechanism is a core wire that is placed within the volume of the foam implant and the implant is crimped over the core wire to create friction between the implant and core wire. The friction allows retraction and advancement of the device until it is fully expanded in the lumen of the treatment vessel. Once the device is fully expanded the friction is reduced enough to allow the core wire to be retracted through the volume of the device.

United States Patent Application 20190015108 describes another delivery mechanism where the device is simply advanced through the catheter with a guidewire or pusher mechanism until the device is completely ejected from the delivery catheter. Another delivery mechanism is one in which the proximal end of the device is attached to a pusher mechanism via an exposed stainless steel wire. When the device is delivered to the target vessel, an electrical current is applied to the pusher mechanism which causes electrolysis of the exposed stainless steel wire-effectively releasing the implant from the pusher mechanism.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIGS. 3A, 3B, 3C respectively illustrate embodiments of a distal pushwire (having a ball tip on the proximal and a sidewall aperture on the implant side), pusher shaft (with a retention pin (dark circle) to retain the collar, internal leaf spring interference where leaf spring interferes with axial aperture on the implant side), and proximal implant collar (with a tapered collar having a through hole to mate with the retention pin of the pusher shaft). FIGS. 3D, 3E, 3F, 3G, and 3H illustrate an embodiment in various stages of device deployment.

FIGS. 4A, 4B illustrate an embodiment in various stages of device deployment.

DETAILED DESCRIPTION

Figure 1:
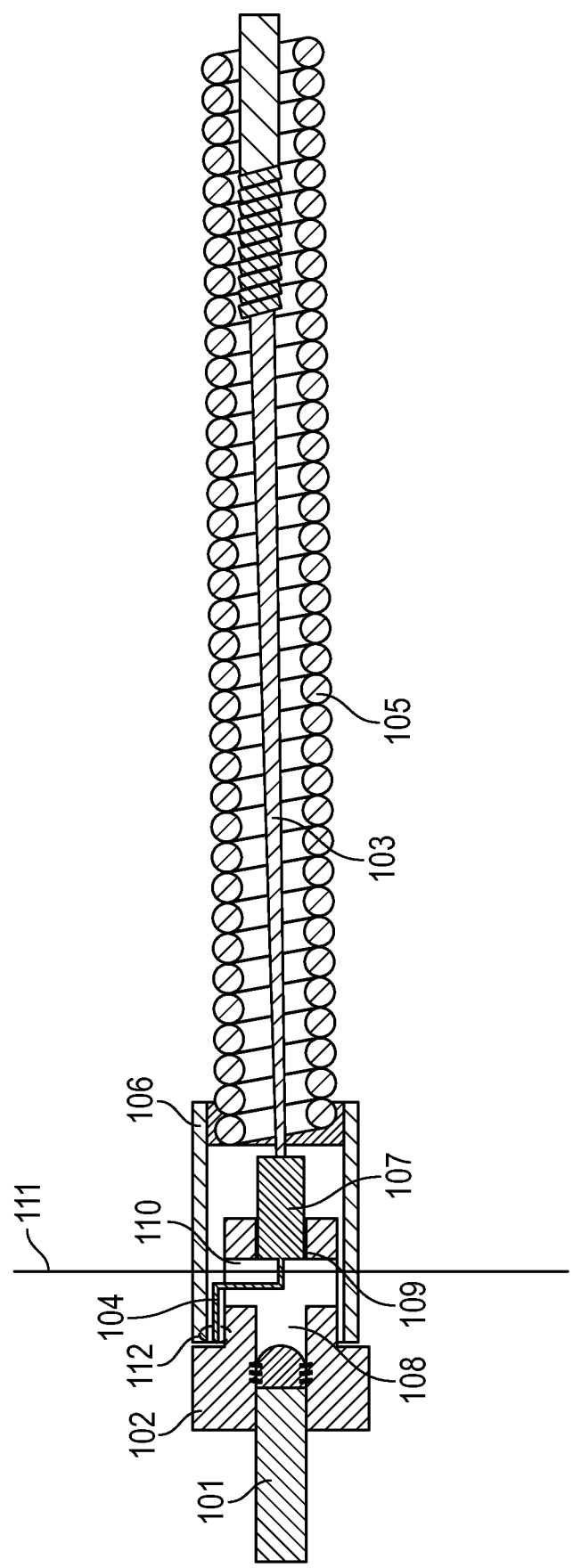
FIG. 1 depicts an embodiment of a mechanical release system. The embodiment includes a wire "S" curve having interference with a side wall aperture on the implant side. The embodiment also has radial interference with the pull wire.

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photomicrograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Phrases such as "comprising at least one of A and B" include situations with A, B, or A and B.

An embodiment includes a system that allows a transcatheter-delivered implant to be advanced and retracted when inside a catheter or delivery sheath, as well as after deployment from the catheter/sheath. The system includes a mechanism that allows the implant to be immediately released in the target location upon activation. Thus, such a system has advantages over above-mentioned systems that rely on, for example, electrolysis as a release mechanism. Such advantages include a faster release, a tactile sensation for the user during release, and ease of manufacture.

Embodiments have the ability to advance and retract a transcatheter-delivered implant prior to delivery to the target site. Then instantaneous detachment of the implant occurs when desired. This increases the safety and comfort of delivering and manipulating minimally invasive implants.

Some embodiments are comprised of an interference fit between the implant and delivery system during final assembly, which allows the implant to be pushed and pulled until the physician wants to release the implant. Such embodiments contain a means of removing the interference fit either by unsheathing the delivery sheath or by pulling a release wire, which effectively delivers the implant instantaneously Embodiments may be used to deliver transcatheter medical implants and allow for device manipulation prior to release. Alternative uses would be to deliver any device through a needle, sheath, catheter, arthroscopic procedure, or other methodology where space is limited. Embodiments may be used by, for example, vascular surgeons, interventional radiologists, and cardiothoracic surgeons.

Embodiments have increased tensile strength in the delivery system, which may help prevent premature detachment, and the design of the interlocking components may result in more reliable detachment. Embodiments maintain control of an implant in both compression and tension until delivery of the implant is desired.

Example 1

Example 1 includes a system comprising an implant that includes a shape memory polymer (SMP) (101) and a collar (102). The system further includes first (103) and second (104) wires and a coil (105) that includes the first wire. Wire 104 may be a flat retention wire. Wire 103 may be a round wire. The system includes a first conduit (106) that (a) is coupled to the coil, and (b) includes the second wire. Conduit 106 may be a radiopaque band that includes platinum and/or iridium (e.g., an alloy or combination of platinum and/or iridium). Other embodiments may have a radiopaque band that includes platinum and/or tungsten (e.g., an alloy or combination of platinum and/or tungsten). The band may include stainless steel or other materials. The system further includes a second conduit (107) that couples the first wire to the second wire. At least a portion of the collar is between the SMP and the coil. The collar includes a channel (108), a first aperture (109) in a first sidewall of the collar, and a second aperture (110) in a second sidewall of the collar. The channel couples the first aperture to the second aperture. The channel may be a through hole in the collar. The second wire is: (a) included within the channel, (b) traverses the second sidewall aperture, and (c) is between the collar and the first conduit.

For example, in FIG. 1 the embodiment includes an implant that includes a SMP foam and a collar. The entire implant is detached from the delivery coil. The delivery mechanism may include a first wire, such as a round wire, and a second wire, such as a flat retention wire. The coil may include the first wire. A first conduit, such as platinum/iridium, platinum/tungsten, or stainless steel band, (a) is coupled to the coil, and (b) includes the second wire. A second conduit, such as a centering hypotube, couples the first wire to the second wire. At least a portion of the collar is between the SMP and the coil. The collar includes a channel, a first aperture in a first sidewall of the collar, and a second aperture in a second sidewall of the collar. The channel couples the first aperture to the second aperture. The second wire is: (a) included within the channel, (b) traverses the second sidewall aperture, and (c) is between the collar and the first conduit.

As used herein, a "hypotube" may be considered broadly as a conduit. The conduit may include metal but is not restricted to metals only and may include polymers and the like. The conduit need not be a tube. The conduit, as used herein, may be hollow or solid along some or all of its length. For example, the conduit may include a long axis and a plane, which is orthogonal to that long axis, may not necessarily intersect an outer perimeter of the tube that is contiguous. For example, the slot may have a cross-section profile of a "U" and the like.

Example 2

The system of example 1, wherein the second wire is included within the first aperture.

Example 3

The system of example 2, wherein: a first plane (111) intersects the first conduit, the second wire, the collar, and the second aperture. The first plane does not intersect the first aperture.

For example, see the "first plane" on FIG. 1.

Example 4

The system of example 3 wherein: the second wire is coupled between the first conduit and the collar via a resistance fit (112). The resistance fit is removed when the first wire is moved proximally and away from the collar. The implant is deployed from the first conduit when the resistance fit is removed.

Figure 2A:
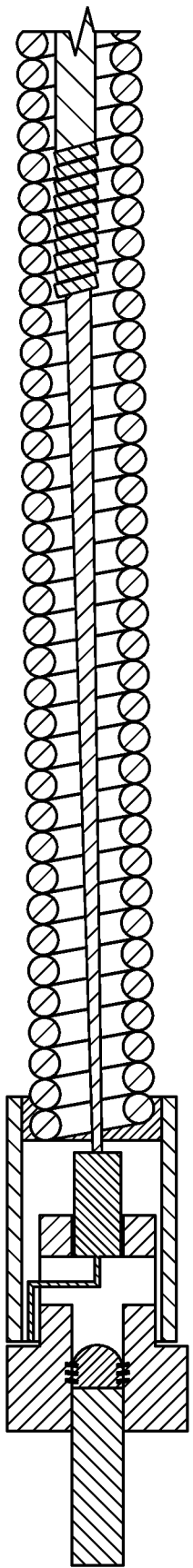
FIGS. 2A, 2B, 2C illustrate an embodiment in various stages of device deployment.
Figure 2B:
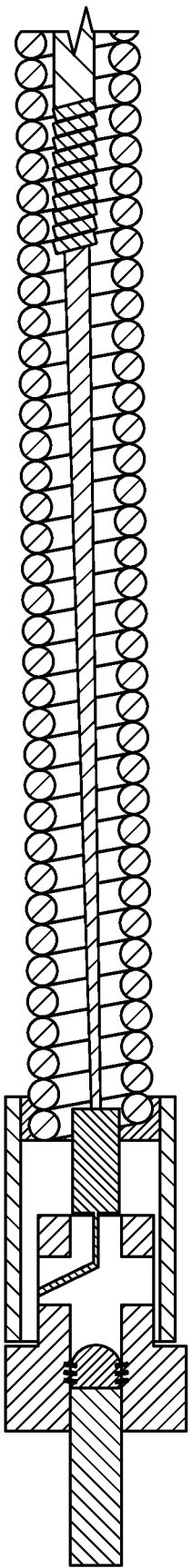
Figure 2C:
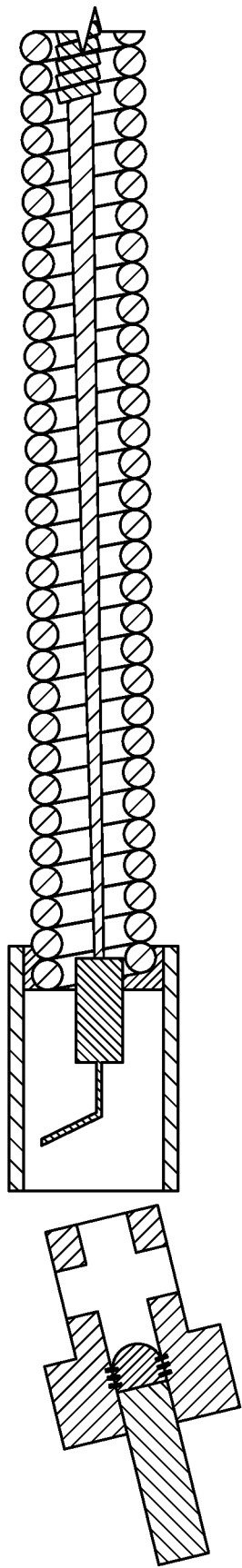

See, for example, FIGS. 2A, 2B, 2C for the area of "resistance fit". A "resistance fit" provides enough resistance such that a physician can move the entire system back and forth (proximally and distally) repeatedly before final deployment of the implant without prematurely having the implant disconnect from the delivery coil. However, when a physician holds the coil steady but pulls proximally on the round wire linkage, the resistance will be overcome and the retention wire will withdraw from the area of impingement that causes the resistance fit. While the circle area in FIG. 1 shows one area of resistance, resistance may be generated at other areas of the retention wire such as within the second aperture.

Example 5

An embodiment includes a system comprising an implant that includes a SMP (501) and a collar (502). The system includes first (503) and second (504) wires, a coil (506) that includes the first wire, and a first conduit (507) that: (a) is coupled to the coil, and (b) includes the second wire. The system includes a second conduit (508) that couples the first wire to the second wire. At least a portion of the collar is between the SMP and the coil. The collar includes a first aperture (509) in a sidewall of the collar. The second wire: (a) is included within the first aperture, (b) traverses an opening to the first aperture, and (c) is between the collar and the first conduit.

For example, see FIG. 5. The SMP may be a SMP foam with a secondary shape and a primary shape wherein the foam may be configured to transition from the secondary shape to the primary shape based on exposure to heat. The first wire may include the "pull wire" and the second wire may include a flattened wire. The embodiment may include a first conduit, such as the chamfered band. The second conduit may include the hypotube that is used to center the system. The first aperture may include a thru hole. However, in some embodiments the first aperture may not necessarily traverse the collar. As shown in FIG. 5, the second wire (a) is included within the first aperture, (b) traverses an opening to the first aperture, and (c) is between the collar and the first conduit.

Coil 506 may include a polyimide. Wire 503 may include a stainless steel pull wire. Conduit 508 may include a centering hypotube. Wires 504, 505 may include flattened stainless steel or Nitinol wires. Band 507 may include a chamfer. The system's chamfer and retention wires force the implant forward and down in the terrestrial frame of FIG. 4B. This causes the foam to move towards the vessel wall (FIG. 5D) in some vascular embodiments. In other words, the arrow pointing to the right would be a pure distal motion but the chamfered system would instead drive the implant downwards as it moves distally. Apertures 509, 510 may include drilled through holes on the collar. Collar 502 may be radiopaque and may include platinum and/or iridium (e.g., an alloy or combination of platinum and/or iridium). Other embodiments may have a radiopaque collar that includes platinum and/or tungsten (e.g., an alloy or combination of platinum and/or tungsten). The band may include stainless steel or other materials. In another embodiment the collar includes stainless steel.

Figure 5A:
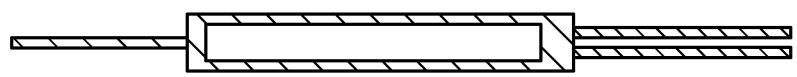
FIGS. 5A, 5B, 5C, 5D illustrate an embodiment in various stages of device deployment.
Figure 5B:
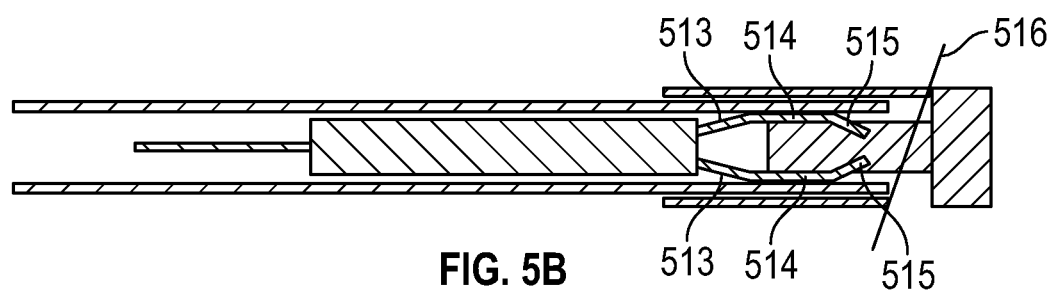
Figure 5C:
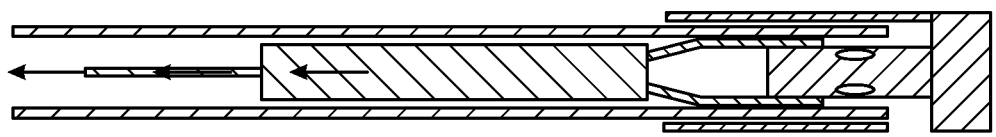
Figure 5D:
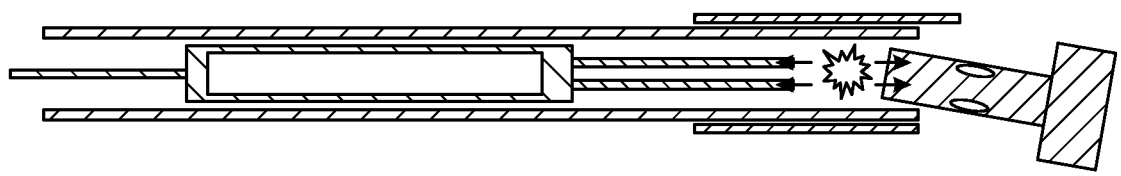

FIG. 5A-5D depict an embodiment where the SMP foam is not shown to place focus on the collar and generally delivery system. The embodiment of FIGS. 5A-5D is similar to the embodiment of FIGS. 4A-4B. However, in FIGS. 5A-5D the natural state of the retention wires is linear. FIG. 5A shows flattened wires are attached to a centering hypotube either by soldering or welding. FIG. 5B shows when the attachment junction is assembled, there are several forces (compressive forces 513, friction forces 514, retention forces 515) that are introduced to the assembly. FIG. 5B further shows chamfer 516. FIG. 5C shows during activation, as the bent tips of the flattened wires separate from the drilled through holes; friction force begins to build in addition to the compression force from the two flattened wires trying to go back to their initial state. The chamfered stainless steel band is restricting the collar from following the "pulled" direction. FIG. 5D shows when separation between the pull wire and the implant collar occurs the compression force is applied to the implant collar, freeing the collar from its containment.

Example 6

The system of example 5 wherein a distal most edge of the first conduit is chamfered.

A chamfer includes a beveled edge such as the edge in FIG. 5.

Example 7

The system of example 5 wherein: a distal most edge of the first conduit includes first (511) and second (512) portions. The first portion is more distal than the second portion.

See, e.g., FIG. 4A regarding the first and second portions.

Example 8

The system of example 7 wherein: the first and second portions form opposing edges of an aperture. The aperture has an opening that is defined by the first and second portions.

For example, the aperture is the area from which a portion of collar is eventually deployed during deployment of the implant for final implantation.

Example 9

The system according to any of examples 5 to 8 comprising a third wire (505), wherein: the first conduit includes the third wire; the second conduit couples the first wire to the third wire; the collar includes a second aperture (510) in the sidewall of the collar. The third wire (a) is included within the second aperture, (b) traverses an opening to the second aperture, and (c) is between the collar and the first conduit.

The "third wire" may be the second of two or more wires (504, 505) and may include flattened stainless steel or a Nitinol wire. Not all embodiments require two retention wires. Some embodiments may include only one retention wire while others may include 3, 4, 5 or more retention wires.

Example 10

The system of example 9 wherein a through-hole traverses the collar and couples the first aperture to the second aperture.

For some embodiments a hole goes through an entire portion of collar while in other embodiments the aperture or apertures may be mere indentions or recesses in a portion of the collar.

Example 10.1

The system of example 9 wherein: a majority of the second wire is included in a plane. A majority of the third wire is included in the plane.

This arrangement helps generate enough retention force to alleviate or lessen the odds that the implant will prematurely separate from the delivery coil before the physician pulls on the pull wire.

Example 10.2

The system of example 10.1 wherein: the first wire includes a long axis. The plane is substantially parallel to the long axis of the first wire.

Example 10.3

The system of example 9 wherein each of the second and third wires are flattened.

Flattening one or both of the second and third wires in some embodiments helps limit the profile of the delivery system. For example, the maximum outer dimeter (see FIG. 5) may be lowered. For example, in an embodiment the wires are non-circular in cross-section. For example, using the X, Y, Z coordinate system on FIG. 5 the wires may be wider in the Z direction than they are tall in the Y direction.

Example 11

The system of example 5 wherein the first aperture includes a through-hole that traverses the collar.

Example 12

The system of example 9 wherein: in a first orientation the collar and the SMP are secured to the first wire via the inclusion of the second wire within the first aperture. In a second orientation the collar and the SMP are no longer secured to the first wire in response to the first and second wires being pulled proximally and the second wire being withdrawn from the first aperture.

In the embodiment of FIG. 5, as the pull wire is pulled proximally to release the implant there is some level of resistance between the retaining second and third wires and the collar. This resistance may cause the implant itself to move proximally and pivot about the first portion of the distal most edge and towards the second portion of the distal most edge. As a result, a proximal portion of the collar moves proximally. To the extent there is a "release" or surge or thrust of the foam when the retention wires (second and third wires) no longer pull the collar proximally, the foam will be thrust slightly away from the "first portion of the dismal most edge" and possibly towards a vessel wall. In other words, instead of the foam being projected distally (see FIG. 5) the foam is instead projected towards a vessel wall, which will immediately stop the progress of the foam. Consequently, the foam will not be displaced to a great extent from where the physician located the foam before pulling the pull wire. In other words, the chamfer helps keep the foam in place upon release by ensure any thrust of the foam is quickly abated by an adjacent vessel wall.

Other embodiments may work differently. For example, in an embodiment as the pull wire is pulled proximally to release the implant there is some level of resistance between the retaining second and third wires and the collar. However, the first portion of the distal most edge may prevent the collar from moving proximally. Still, the collar needs to be ejected from the coil/delivery system. To that end (see, e.g., FIGS. 5A-5D), as the retention wires release the collar the retention wires may "snap" back to an original state. In doing so, when the retention wire (or wires) snap back to its/their original non-deformed state it/they push the collar out of the coil and first conduit. This solves the issue of how to get the collar deployed while still ensuring the implant is not released prematurely. Put another way, the retention wires may supply both a resistive fit (e.g., between the collar and coil) and a compressive force (e.g., the wires pressing into apertures of the collar), to keep the implant from prematurely releasing while a physician moves the implant back and forth seeking the final deployment site. Those same wires that hold the collar within the delivery system to prevent premature deployment can also help push the collar out of the delivery system due to their transformation from a deformed state to a non-deformed state.

While some embodiments may include the chamfer on the first conduit, other embodiments have no such requirement. A physician may prefer, for example, a non-chamfered option for one type of case (e.g., deploying a foam into a cranial aneurysm) and a chamfered option for another type of case (e.g., deploying a foam into a vessel in the thigh). The need for a chamfer may also vary depending on the projection force, if any, generated by retention wires. For example, a smaller projection force may not necessitate a chamfered option. In some embodiments the retention wires may exert little to no projection force on the implant. For example, in some embodiments once retention wires have been withdrawn the amount of remaining friction force exerted on the collar by the delivery system may be so small that, for example, blood embolizing within the SMP foam (or other embolic device) may generate enough resistance on the implant such that the delivery system can be withdrawn without moving the implant from its desired implant position. Such a low propulsion force may be desirable in some cases, such as placing a foam in a cranial aneurysm, where vessel walls may be thinner (and less tolerant of an embolic element being propelled from the delivery system) than a vessel wall of a peripheral vessel in the thigh.

Example 13

The system of example 12 wherein the second wire is resilient.

For example, nitinol is considered "resilient".

Example 14

The system of example 13 wherein the second wire includes at least one of stainless steel, nickel titanium, or combinations thereof.

Example 14.1

The system of example 12 wherein the second wire has shape memory.

Shape memory is the ability of, for example, Nitinol to undergo deformation at one temperature, stay in its deformed shape when the external force is removed, then recover its original, undeformed shape upon heating above its "transformation temperature".

Example 14.2

The system of example 12 wherein the second wire has superelasticity.

Superelasticity is the ability for the metal to undergo large deformations and immediately return to its undeformed shape upon removal of the external load. These materials can withstand high strains without plastic deformation. For example, Nitinol can deform 10-30 times as much as ordinary metals and return to its original shape.

Example 14.3

The system of example 12 wherein the second wire has at least one of shape memory or superelasticity.

Example 14.4

The system of example 14.3, wherein: the second wire has a deformed state and a non-deformed state; in the deformed state the second wire is non-linear; in the non-deformed state the second wire is linear.

Example 14.5

The system of example 14.4, wherein the second wire is in the deformed state and at least a portion of the second wire is included within the first aperture.

Example 14.6

The system of example 14.5, wherein the second wire is in the deformed state and includes at least one curved portion that curves around a portion of the collar and into the first aperture.

Embodiments are not limited to the shapes of retention wires seen in FIGS. 4A-5D. For example, some embodiments include two wires that collectively form a "V" shape. The spacing between the wires may limit force with which the implant is projected from the delivery system.

Example 14.7

The system of example 14.3, wherein: the second wire has a deformed state and a non-deformed state; the second wire is in the deformed state.

Example 14.8

The system of example 14.7, wherein in the deformed state the second wire generates; (a) friction force between the collar and the first conduit, and (b) compressive force upon the collar.

Example 14.90

The system of example 14.8 wherein: when transitioning from the first orientation to the second orientation the second and third wires transition from the deformed state to the non-deformed state. The collar is thrust away from the first conduit in response to the second and third wires transitioning from the deformed state to the non-deformed state.

Example 14.91

The system of example 14.90 wherein: the first wire includes a long axis. The collar is thrust away from the first conduit along a direction in response to the second and third wires transitioning from the deformed state to the non-deformed state. The direction is non-parallel to the long axis of the first wire.

In an embodiment, as the retention wires are pulled proximally, they pull the collar proximally. However, the chamfer causes the implant to be subjected to a rotational force about the distal most edge of the chamfer. As the retention wires snap back into their initial state, they provide a pushing force that pushes the implant away from the delivery system at an angle that pushes the implant to the side and not directly in line with a long axis of the coil and/or first wire. Please note how the implant is rotated downward in the bottom depiction of FIG. 5D.

Example 15

An embodiment includes a system comprising: an implant that includes a SMP and a base, the SMP and the base being permanently affixed to one another. The system includes a linkage; a first resilient metal member; a first conduit that includes the linkage; and a second conduit that: (a) is coupled to the first conduit, and (b) includes the first resilient metal member. The linkage is coupled to the first resilient metal member. At least a portion of the base is between the SMP and a portion of the first conduit. The base includes a first aperture in a sidewall of the base. The first resilient metal member: (a) is included within the first aperture, (b) traverses an opening to the first aperture, and (c) is between the base and the second conduit.

Thus, not all embodiments are disclosed in FIG. 5. For example, the "centering hypo" tube may or may not be included in some embodiments.

Example 15.1

The system of example 15 wherein the linkage includes at least one of a cord, cable, line, string, rod, wire, bar, coil, or combinations thereof.

Example 16

The system of example 15 wherein a distal most edge of the second conduit is chamfered.

Example 17

The system of example 15 wherein: a distal most edge of the second conduit includes first and second portions. The first portion is more distal than the second portion.

Example 18

The system of example 17 wherein the first and second portions form opposing edges of an aperture. The aperture has an opening that is defined by the first and second portions.

Example 19

The system according to any of examples 15 to 18 comprising a second resilient metal member. The second conduit includes the second resilient metal member. The linkage is coupled to the second resilient metal member. The base includes a second aperture in the sidewall of the base. The second resilient metal member (a) is included within the second aperture, (b) traverses an opening to the second aperture, and (c) is between the base and the second conduit.

Example 20

The system of example 19 wherein a through-hole traverses the base and couples the first aperture to the second aperture.

Example 20.1

The system of example 19 wherein: a majority of the first resilient metal member is included in a plane. A majority of the second resilient metal member is included in the plane.

Example 20.2

The system of example 20.1 wherein: the linkage includes a long axis. The plane is substantially parallel to the long axis of the linkage.

Example 20.3

The system of example 19 wherein each of the first and second resilient metal members is flattened.

Example 21

The system of example 15 wherein the first aperture includes a through-hole that traverses the base.

Example 22

The system of example 19 wherein: in a first orientation the base and the SMP are secured to the linkage via the inclusion of the first resilient metal member within the first aperture. In a second orientation the base and the SMP are no longer secured to the linkage in response to the linkage and the first resilient metal member being pulled proximally and the first resilient metal member being ejected from the first aperture.

Example 23

The system of example 22 wherein the first resilient metal member includes at least one of stainless steel, nickel titanium, or combinations thereof.

Example 24.1

The system of example 22 wherein the first resilient member has shape memory.

Example 24.2

The system of example 22 wherein the first resilient member has superelasticity.

Example 24.3

The system of example 22 wherein the first resilient member has at least one of shape memory or superelasticity.

Example 24.4

The system of example 24.3, wherein: the first resilient member has a deformed state and a non-deformed state. In the deformed state the first resilient member is non-linear. In the non-deformed state, the first resilient member is linear.

Example 24.5

The system of example 24.4, wherein the first resilient member is in the deformed state and at least a portion of the first resilient member is included within the first aperture.

Example 24.6

The system of example 24.5, wherein the first resilient member is in the deformed state and includes at least one curved portion that curves around a portion of the collar and into the first aperture.

Example 24.7

The system of example 24.3, wherein: the first resilient member has a deformed state and a non-deformed state. The first resilient member is in the deformed state.

Example 24.8

The system of example 24.7, wherein in the deformed state the first resilient member generates: (a) friction force between the base and the second conduit, and (b) compressive force upon the base.

Example 24.90

The system of example 24.8 wherein: when transitioning from the first orientation to the second orientation the first and second resilient member transition from the deformed state to the non-deformed state. The base is thrust away from the second conduit in response to the first and second resilient members transitioning from the deformed state to the non-deformed state.

Example 24.91

The system of example 24.90 wherein: the linkage includes a long axis. The base is thrust away from the second conduit along a direction in response to the first and second resilient members transitioning from the deformed state to the non-deformed state. The direction is non-parallel to the long axis of the linkage.

Example 25

An embodiment includes a system comprising: an implant that includes a shape memory polymer (SMP) and a base. The SMP and the base are permanently affixed to one another. The system includes a linkage; a first resilient metal member; a first conduit that includes the linkage; and a second conduit that: (a) is coupled to the first conduit, and (b) includes the first resilient metal member. The linkage is coupled to the first resilient metal member and at least a portion of the base is between the SMP and a portion of the first conduit. The base includes a first aperture in a sidewall of the base. The first resilient metal member: (a) is included within the first aperture, (b) traverses an opening to the first aperture, and (c) is between the base and the second conduit.

Example 25.1

The system of example 15 wherein the linkage includes at least one of a cord, cable, line, string, rod, wire, bar, coil, or combinations thereof.

Example 26

The system according to any of examples 25 to 25.1 wherein a distal most edge of the second conduit is chamfered.

Example 27

The system according to any of examples 25 to 25.1 wherein: a distal most edge of the second conduit includes first and second portions. The first portion is more distal than the second portion.

Example 28

The system of example 17 wherein: the first and second portions form opposing edges of an aperture. The aperture has an opening that is defined by the first and second portions.

Example 29

The system according to any of examples 25 to 28 comprising a second resilient metal member. The second conduit includes the second resilient metal member. The linkage is coupled to the second resilient metal member and the base includes a second aperture in the sidewall of the base. The second resilient metal member (a) is included within the second aperture, (b) traverses an opening to the second aperture, and (c) is between the base and the second conduit.

Example 30

The system of example 29 wherein a through-hole traverses the base and couples the first aperture to the second aperture.

Example 30.1

The system according to any of examples 28 to 29 wherein: a majority of the first resilient metal member is included in a plane. A majority of the second resilient metal member is included in the plane.

Example 30.2

The system of example 30.1 wherein the linkage includes a long axis and the plane is substantially parallel to the long axis of the linkage.

Example 30.3

The system according to any of examples 29 to 30.2 wherein each of the first and second resilient metal members is flattened.

Example 31

The system according to any of examples 25 to 30.3 wherein the first aperture includes a through-hole that traverses the base.

Example 32

The system according to any of examples 25 to 31 wherein: in a first orientation the base and the SMP are secured to the linkage via the inclusion of the first resilient metal member within the first aperture. In a second orientation the base and the SMP are no longer secured to the linkage in response to the linkage and the first resilient metal member being pulled proximally and the first resilient metal member being ejected from the first aperture.

Example 33

The system according to any of examples 25 to 32 wherein the first resilient metal member includes at least one of stainless steel, nickel titanium, or combinations thereof.

Example 35

An embodiment includes a system comprising an implant that includes an expandable embolic element and a base. The expandable embolic element and the base are permanently affixed to one another. The system includes a linkage; a first resilient member; a first conduit that includes the linkage. The linkage is coupled to the first resilient metal member; at least a portion of the base is between the expandable embolic element and a portion of the first conduit; the base includes a first aperture in a sidewall of the base; the first resilient metal member: (a) is included within the first aperture, and (b) traverses an opening to the first aperture.

Example 35.1

The system of example 35 wherein the linkage includes at least one of a cord, cable, line, string, rod, wire, bar, coil, or combinations thereof.

Example 36

The system according to any of examples 35 to 35.1 wherein a distal most edge of the first conduit is chamfered.

Example 37

The system according to any of examples 35 to 35.1 wherein: a distal most edge of the first conduit includes first and second portions; the first portion is more distal than the second portion.

Example 38

The system of example 37 wherein: the first and second portions form opposing edges of an aperture; the aperture has an opening that is defined by the first and second portions.

Example 39

The system according to any of examples 35 to 38 comprising a second resilient metal member, wherein: the linkage is coupled to the second resilient metal member; the base includes a second aperture in the sidewall of the base; the second resilient metal member (a) is included within the second aperture, and (b) traverses an opening to the second aperture.

Example 40

The system of example 39 wherein a through-hole traverses the base and couples the first aperture to the second aperture.

Example 40.1

The system according to any of examples 38 to 39 wherein: a majority of the first resilient metal member is included in a plane. A majority of the second resilient metal member is included in the plane.

Example 40.2

The system of example 40.1 wherein: the linkage includes a long axis. The plane is substantially parallel to the long axis of the linkage.

Example 40.3

The system according to any of examples 39 to 40.2 wherein each of the first and second resilient metal members is flattened.

Example 41

The system according to any of examples 35 to 40.3 wherein the first aperture includes a through-hole that traverses the base.

Example 42

The system according to any of examples 35 to 41 wherein: in a first orientation the base and the expandable embolic element are secured to the linkage via the inclusion of the first resilient metal member within the first aperture. In a second orientation the base and the expandable embolic element are no longer secured to the linkage in response to the linkage and the first resilient metal member being pulled proximally and the first resilient metal member being ejected from the first aperture.

Example 43

The system according to any of examples 35 to 42 wherein the first resilient metal member includes at least one of stainless steel, nickel titanium, or combinations thereof.

Example 1a

An embodiment includes a system comprising an implant including a SMP (701) non-releasably coupled to a collar (702). The system includes a distal actuator wire (703), a retention wire (704), a proximal actuator wire (705), and a shaft (706) that couples the distal actuator wire to the proximal actuator wire. The system further includes a coil (707) (e.g., stainless steel coil) that includes the distal actuator wire but not the retention wire. The system further includes a first conduit (708) (a) releasably coupled to the collar, and (b) including the distal actuator wire and the retention wire but not the coil. The system includes a second conduit (709) (a) releasably coupled to the collar, and (b) including the distal actuator wire, the retention wire, and the coil. The collar includes a channel (710), a first aperture (711), and a second aperture (712) that is located in a sidewall (713) of the collar. The distal actuator wire is: (a) included within the channel, and (b) traverses the first aperture but not the second aperture. The retention wire is: (a) included within the channel, and (b) traverses the first and second apertures.

Figure 7A:
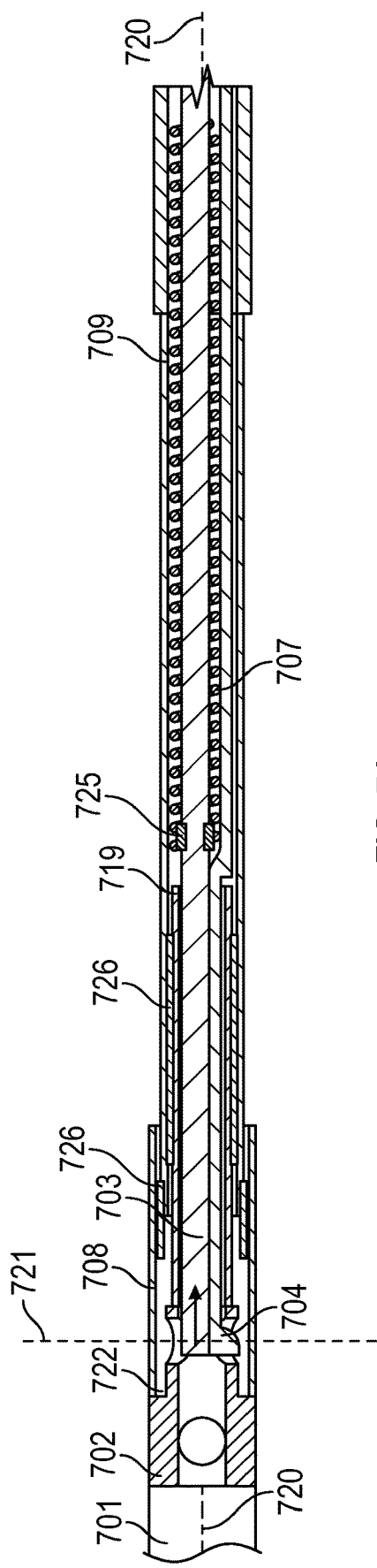
FIG. 7A, 7B, 7C, 7D, 7E, 7F, 7G, 7H illustrate an embodiment in various stages of device deployment.
Figure 7B:
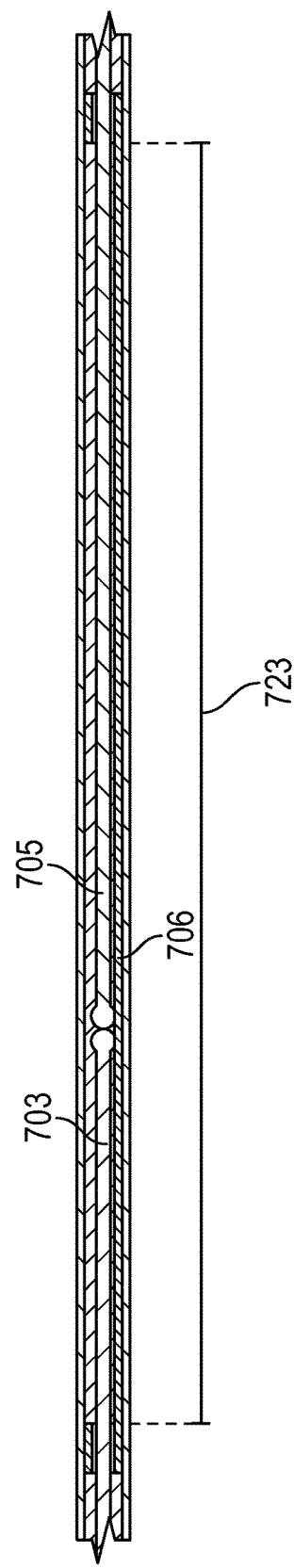
Figure 7C:
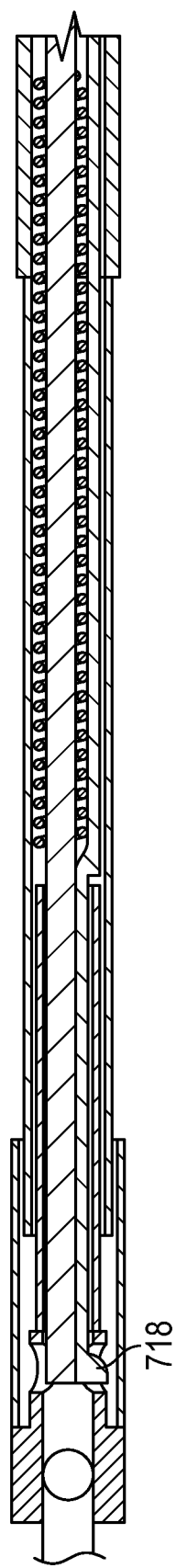

Adhesive couplings 725 and solder bond 725 are shown in FIG. 7A but not other figures to promote clarity. Wires 703, 704 may include stainless steel and the like.

Example 2a

The system of example 1a, wherein the shaft includes a distal aperture (714) that includes the distal actuator wire and a proximal aperture (715) that includes the proximal actuator wire.

The apertures of the shaft may include an opening, gap, cuff, slot, groove, thru-hole (e.g., a hole that goes completely across an object such as a plug), and the like. Rod or shaft 706 may include stainless steel.

Example 3a

The system of example 2a, wherein the distal aperture is slidably coupled to the distal actuator wire and the proximal aperture is slidably coupled to the proximal actuator wire.

In an embodiment only one of the distal or proximal apertures is included in the system. Such a singular aperture may not necessarily be included in the proximal or distal areas of the shaft or wire.

Example 4a

The system of example 3a, wherein: a proximal portion (716) of the distal actuator wire is proximal to the distal aperture and has an outer diameter that is larger than an inner diameter of the distal aperture. A distal portion (717) of the proximal actuator wire is distal to the proximal aperture and has an outer diameter that is larger than an inner diameter of the proximal aperture.

Example 5a

The system of example 4a, wherein in a non-deployed configuration the proximal portion of the distal actuator wire does not directly contact the distal aperture of the shaft. In a deployed configuration the proximal portion of the distal actuator wire directly contacts the distal aperture of the shaft.

Figure 7D:
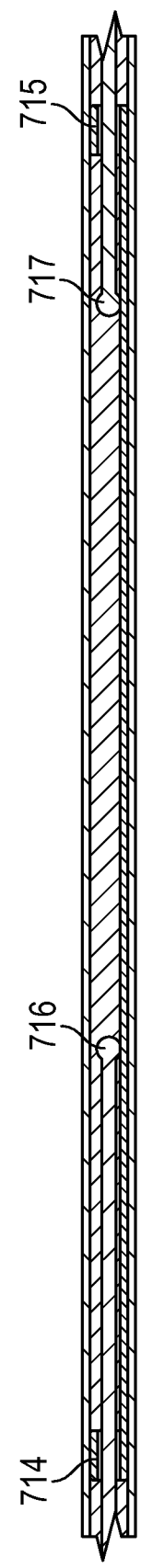
Figure 7E:
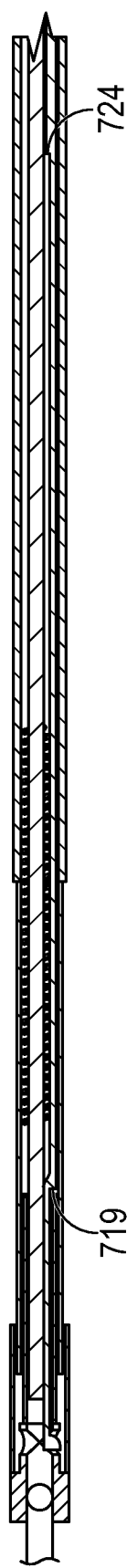
Figure 7F:
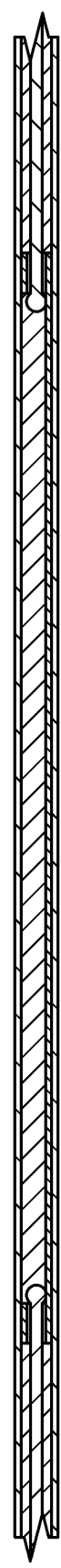

For example, FIG. 7D shoes a non-deployed configuration and FIG. 7F shows a deployed configuration. In FIG. 7D the proximal actuator wire can freely move without impacting the distal actuator wire. The distal actuator wire is responsible for relieving the interference between the distal actuator wire and the retention wire.

Figure 6:
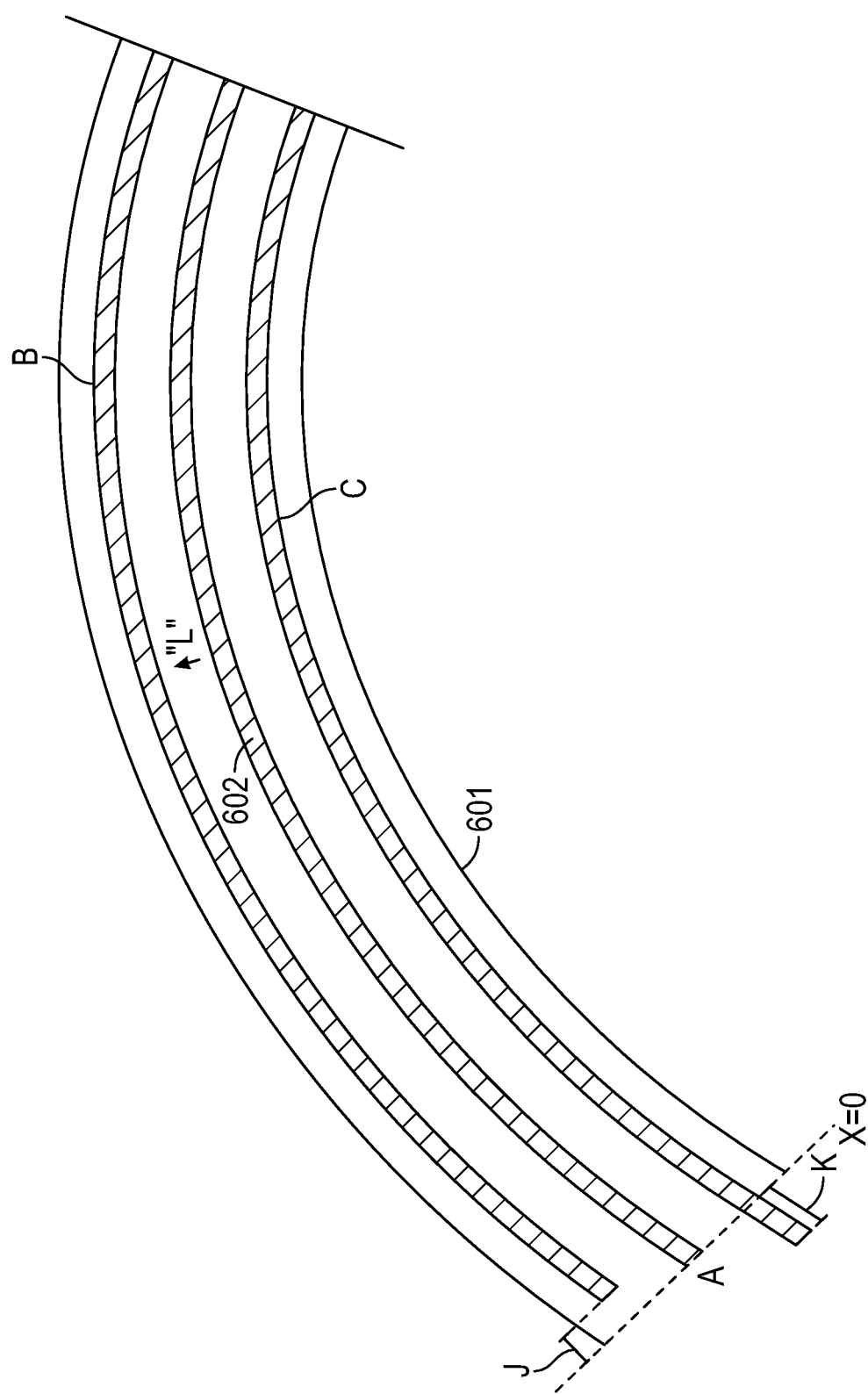
FIG. 6 illustrates problems with a single pull-wire system.

FIG. 6 shows a problem several embodiments described herein address. Such problems exist with many conventional single pull wire systems. Specifically, conduit 601 includes an actuator wire 802 that would couple to a medical device implant. The wire has length (L) when it is not bent. Such bending can occur when traversing a patient's vasculature. However, that same wire can potentially shorten if it takes the outer radius (B), retracting the wire from its distal origin position (x=0) by a distance "j". Further, that same wire can potentially lengthen if it takes the inner radius (C), elongating the wire from its distal origin position (x=0) by a distance "k". This variable distance can affect the accuracy and comfort level of the physician implanting the device and this variability is lowered in embodiment that allow for bending to be "broken up" due to the sliding cuffs 714, 715.

In an embodiment wire 706 is omitted and cuff/aperture 714 is instead at the location of bead 717. This provides a two-wire embodiment (wires 703, 705) instead of a three-wire embodiment (wires 703, 705, 706).

Example 6a

The system of example 5a, wherein: in the non-deployed configuration the distal portion of the proximal actuator wire does not directly contact the proximal aperture of the shaft. In the deployed configuration the distal portion of the proximal actuator wire directly contacts the proximal aperture of the shaft.

Example 7a

The system of example 6a, wherein: the retention wire has a proximal projection (724) that is proximal to at least a portion of the coil. In the non-deployed configuration, the proximal projection does not directly contact the coil. In the deployed configuration the proximal projection directly contacts the coil.

For example, in FIG. 7E partial actuation/deployment of the distal actuator wire has occurred. The actuator coil has not yet engaged with the retention wire proximal tab 724. This coil/proximal tab engagement allows the physician to directly pull the retention wire and deploy the implant. This "direct activation" gives more control to the physician regarding deployment of the implant.

In FIG. 7F, both actuator wires are in full tension. The interference of balls 716, 717 with apertures 714, 715 allow the physician to pull the four wires 703, 704, 705, 706 in tension as a 'composite' single wire system. Gap 723 between the cuffs accounts for about, for example, 0.5-2% of wire foreshortening (see radius B of FIG. 6).

Figure 7G:
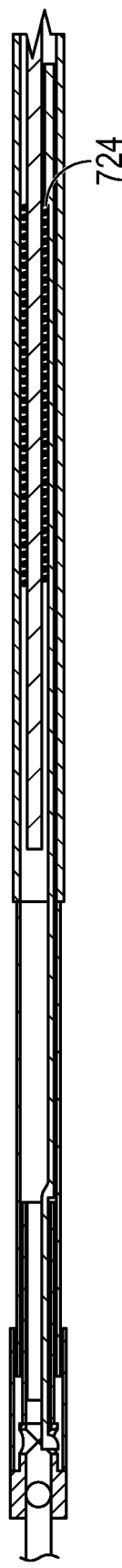
Figure 7H:
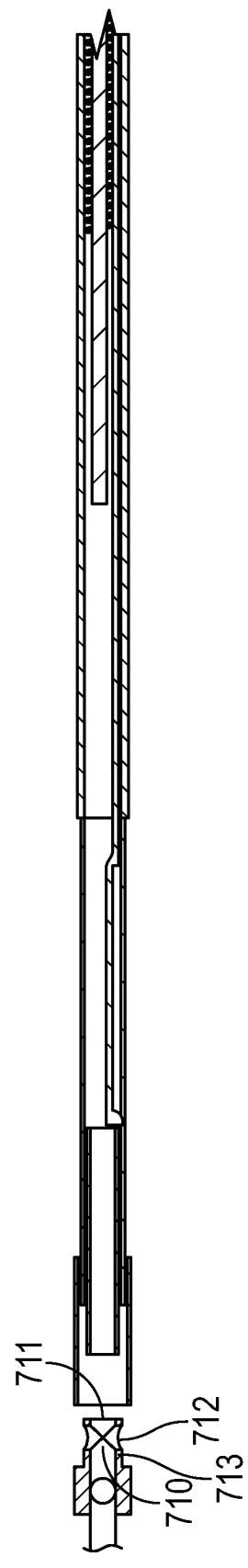

In FIG. 7G, the actuator coil is engaged with proximal tab 724 and the coil will pull the retention wire out of the collar hole 712 and release the implant without further interference. Afterwards, in FIG. 7H the retention wire is fully retracted into lumen 709 (e.g., a polyimide shaft or lumen) upon full actuation. The detachment collar 702 is now able to release from the system. Collar 702 may be radiopaque and include platinum and/or iridium (e.g., an alloy or combination of platinum and/or iridium). Other embodiments may have a radiopaque collar that includes platinum and/or tungsten (e.g., an alloy or combination of platinum and/or tungsten). However, in other embodiments the collar includes stainless steel. Conduit 708 may be radiopaque and include platinum and/or iridium and serve as a distal marker band.

Example 8a

The system of example 2a, wherein the retention wire has a proximal projection (724) that is proximal to at least a portion of the coil.

Example 9a

The system of example 8a, wherein: the retention wire has a distal projection (718) included in the second aperture. The retention wire has a main body and the proximal and distal projections of the retention wire both extend radially away from the main body of the retention wire.

Example 10a

The system of example 9a, wherein: the distal projection of the retention wire has proximal and distal walls. The second conduit includes a long axis (720). The proximal wall of the distal projection of the retention wire is non-orthogonal to the long axis of the second conduit.

Example 11a

The system of example 2a comprising a third conduit (719), wherein: a portion of the third conduit is included within the first conduit but not the second conduit. Another portion of the third conduit is included within the second conduit but not the first conduit.

Conduit 719 may include polyimide and function as an inner stopper.

Example 12a

The system of example 11a, wherein: the third conduit is fixedly coupled to at least one of the first or second conduits. The third conduit is slidably coupled to both of the first and second conduits.

Example 13a

The system of example 2a comprising a void (722) between the collar and the first conduit. The second conduit includes a long axis (720). A first plane (721) is orthogonal to the long axis. The first plane intersects the first conduit, the second aperture, the void, and the retention wire.

Example 14a

The system of example 13a, wherein the first plane intersects the distal actuator wire.

Example 15a

The system of example 13a, wherein the first conduit is more radiopaque than the second conduit.

Example 16a

The system of example 15a, wherein the first conduit includes at least one of platinum, iridium, tungsten, or combinations thereof.

Example 17a

The system of example 1a, wherein the distal actuator wire directly contacts the retention wire and applies a force to maintain the retention wire within the second aperture.

Example 18a

The system of example 1a, wherein the coil is non-releasably coupled to the distal actuation cord.

Example 19a

The system of example 1a, wherein: in a non-deployed configuration the shaft overlaps the distal actuator wire a first overlapping distance. In a deployed configuration the shaft overlaps the distal actuator wire a second overlapping distance that is less the first overlapping distance. The second conduit includes a long axis and the first and second overlapping distances are both parallel to the long axis.

Example 1b

An embodiment includes a system comprising: a medical implant including a channel, a first aperture, and a second aperture that is located in a sidewall of the medical implant. The system includes a first wire, a second wire, a third wire, and a shaft or wire that couples the first wire to the third wire. The system includes a coil that includes the first wire but not the second wire. The system includes a first conduit: (a) releasably coupled to the medical implant, and (b) including the first wire and the second wire but not the coil. The system includes a second conduit: (a) releasably coupled to the medical implant, and (b) including the first wire, the second wire, and the coil. The first wire is: (a) included within the channel, and (b) traverses the first aperture but not the second aperture. The second wire is: (a) included within the channel, and (b) traverses the first and second apertures.

As used herein, a "wire" includes a coupling agent (solid or hollow) such as a cord, conduit (solid or hollow), shaft, rod and the like and has both rigidity (e.g., linear rigidity parallel to and along a long axis of the wire) and flexibility (e.g., radial flexibility orthogonal to a long axis of the wire) with regard to devices that traverse vasculature. Depending on materials used for wires and diameters of wires described herein, the wires may have varying flexibilities. Wires and/or shafts used herein, such as elements 703, 704, 705, 706, may have equivalent or different flexibilities.

Embodiments may be used with SMP foam implants but may be used more generally with medical implants.

Example 2b

The system of example 1b, wherein the shaft or wire includes a distal aperture that includes the first wire and a proximal aperture that includes the third wire.

Example 3b

The system of example 2b, wherein the distal aperture is slidably coupled to the first wire and the proximal aperture is slidably coupled to the third wire.

Example 4b

The system of example 3b, wherein: a proximal portion of the first wire is proximal to the distal aperture and has an outer diameter that is larger than an inner diameter of the distal aperture. A distal portion of the third wire is distal to the proximal aperture and has an outer diameter that is larger than an inner diameter of the proximal aperture.

Example 5b

The system of example 4b, wherein: in a non-deployed configuration the proximal portion of the first wire does not directly contact the distal aperture of the shaft or wire; in a deployed configuration the proximal portion of the first wire directly contacts the distal aperture of the shaft or wire.

Example 6b

The system of example 5b, wherein: in the non-deployed configuration the distal portion of the third wire does not directly contact the proximal aperture of the shaft or wire. In the deployed configuration the distal portion of the third wire directly contacts the proximal aperture of the shaft or wire.

Example 7b

The system of example 6b, wherein: the second wire has a proximal projection that is proximal to at least a portion of the coil. In the non-deployed configuration the proximal projection does not directly contact the coil. In the deployed configuration the proximal projection directly contacts the coil.

Example 8b

The system of example 2b, wherein the second wire has a proximal projection that is proximal to at least a portion of the coil.

Example 9b

The system of example 8b, wherein the second wire has a distal projection included in the second aperture. The second wire has a main body and the proximal and distal projections of the second wire both extend radially away from the main body of the second wire.

Example 10b

The system of example 9b, wherein: the distal projection of the second wire has proximal and distal walls. The second conduit includes a long axis. The proximal wall of the distal projection of the second wire is non-orthogonal to the long axis of the second conduit.

Example 11b

The system of example 2b comprising a third conduit. A portion of the third conduit is included within the first conduit but not the second conduit. Another portion of the third conduit is included within the second conduit but not the first conduit.

Example 12b

The system of example 11b, wherein: the third conduit is fixedly coupled to at least one of the first or second conduits. The third conduit is slidably coupled to both of the first and second conduits.

Example 13b

The system of example 2b comprising a void between the medical implant and the first conduit. The second conduit includes a long axis. A first plane is orthogonal to the long axis. The first plane intersects the first conduit, the second aperture, the void, and the second wire.

Example 14b

The system of example 13b, wherein the first plane intersects the first wire.

Example 15b

The system of example 13b, wherein the first conduit is more radiopaque than the second conduit.

Example 16b

The system of example 15b, wherein the first conduit includes at least one of platinum, iridium, tungsten, or combinations thereof.

Example 17b

The system of example 1b, wherein the first wire directly contacts the second wire and applies a force to maintain the second wire within the second aperture.

Example 18b

The system of example 1b, wherein the coil is non-releasably coupled to the distal actuation cord.

Example 19b

The system of example 1b, wherein: in a non-deployed configuration the shaft or wire overlaps the first wire a first overlapping distance. In a deployed configuration the shaft or wire overlaps the first wire a second overlapping distance that is less the first overlapping distance. The second conduit

Example 1c

An embodiment includes a medical implant delivery system comprising: a first wire, a second wire, a third wire, and a shaft or wire that couples the first wire to the third wire. The system further includes a coil that includes the first wire but not the second wire and a first conduit: (a) to releasably couple to the medical implant, and (b) including the first wire and the second wire but not the coil. The system further includes a second conduit: (a) to releasably couple to the medical implant, and (b) including the first wire, the second wire, and the coil. The first wire is configured to be: (a) included within a channel of the medical implant, and (b) traverse a first aperture of the medical implant but not a second aperture located in a sidewall of the medical implant. The channel is to couple the first aperture to the second aperture. The second wire is configured to be: (a) included within the channel, and (b) traverse the first and second apertures.

Systems may be made, sold, and/or shipped independently of any medical implant (whereby the implant may be joined to the system at a later time).

Example 2c

The system of example 1c, wherein the shaft or wire includes a distal aperture that includes the first wire and a proximal aperture that includes the third wire.

Example 3c

The system of example 2c, wherein the distal aperture is slidably coupled to the first wire and the proximal aperture is slidably coupled to the third wire.

Example 4c

The system of example 3c, wherein: a proximal portion of the first wire is proximal to the distal aperture and has an outer diameter that is larger than an inner diameter of the distal aperture. A distal portion of the third wire is distal to the proximal aperture and has an outer diameter that is larger than an inner diameter of the proximal aperture.

Example 5c

The system of example 4c, wherein: in a non-deployed configuration the proximal portion of the first wire does not directly contact the distal aperture of the shaft or wire. In a deployed configuration the proximal portion of the first wire directly contacts the distal aperture of the shaft or wire.

Example 6c

The system of example 5c, wherein in the non-deployed configuration the distal portion of the third wire does not directly contact the proximal aperture of the shaft or wire. In the deployed configuration the distal portion of the third wire directly contacts the proximal aperture of the shaft or wire.

Example 7c

The system of example 6c, wherein: the second wire has a proximal projection that is proximal to at least a portion of the coil. In the non-deployed configuration the proximal projection does not directly contact the coil. In the deployed configuration the proximal projection directly contacts the coil.

Example 8c

The system of example 2c, wherein the second wire has a proximal projection that is proximal to at least a portion of the coil.

Example 9c

The system of example 8c, wherein: the second wire has a distal projection to be included in the second aperture. The second wire has a main body and the proximal and distal projections of the second wire both extend radially away from the main body of the second wire.

Example 10c

The system of example 9c, wherein: the distal projection of the second wire has proximal and distal walls. The second conduit includes a long axis. The proximal wall of the distal projection of the second wire is non-orthogonal to the long axis of the second conduit.

Example 11c

The system of example 2c comprising a third conduit. A portion of the third conduit is included within the first conduit but not the second conduit. Another portion of the third conduit is included within the second conduit but not the first conduit.

Example 12c

The system of example 11c, wherein the third conduit is fixedly coupled to at least one of the first or second conduits. The third conduit is slidably coupled to both of the first and second conduits.

Example 13c

The system of example 2c comprising a void between the medical implant and the first conduit. The second conduit includes a long axis. A first plane is orthogonal to the long axis. The first plane intersects the first conduit, the void, the second wire, and is configured to intersect the second aperture.

Example 14c

The system of example 13c, wherein the first plane intersects the first wire.

Example 15c

The system of example 13c, wherein the first conduit is more radiopaque than the second conduit.

Example 16c

The system of example 15c, wherein the first conduit includes at least one of platinum, iridium, tungsten, or combinations thereof.

Example 17c

The system of example 1c, wherein the first wire directly contacts the second wire and is configured to apply a force to maintain the second wire within the second aperture.

Example 18c

The system of example 1c, wherein the coil is non-releasably coupled to the distal actuation cord.

Example 19c

The system of example 1c, wherein: in a non-deployed configuration the shaft or wire overlaps the first wire a first overlapping distance. In a deployed configuration the shaft or wire overlaps the first wire a second overlapping distance that is less the first overlapping distance. The second conduit includes a long axis and the first and second overlapping distances are both parallel to the long axis.

Example 1d

An embodiment includes a system comprising: a medical implant including a channel, a first aperture, and a second aperture that is located in a sidewall of the medical implant. The system includes a first wire, a second wire, a third wire, and a shaft or wire that couples the first wire to the third wire. The system includes a first conduit: (a) releasably coupled to the medical implant, and (b) including the first wire and the second wire. The system includes a second conduit: (a) releasably coupled to the medical implant, and (b) including the first wire, and the second wire. The first wire is: (a) included within the channel, and (b) traverses the first aperture but not the second aperture. The second wire is: (a) included within the channel, and (b) traverses the first and second apertures.

Thus, not all embodiments include a coil. For example, the first wire may include projections, shoulders, lips, and the like that cooperate with other system elements to deploy the implant.

Example 2d

The system of example 1d, wherein the shaft or wire includes a distal aperture that includes the first wire and a proximal aperture that includes the third wire.

Example 3d

The system of example 2d, wherein the distal aperture is slidably coupled to the first wire and the proximal aperture is slidably coupled to the third wire.

Example 4d

The system of example 3d, wherein: a proximal portion of the first wire is proximal to the distal aperture and has an outer diameter that is larger than an inner diameter of the distal aperture. A distal portion of the third wire is distal to the proximal aperture and has an outer diameter that is larger than an inner diameter of the proximal aperture.

Example 5d

The system of example 4d, wherein: in a non-deployed configuration the proximal portion of the first wire does not directly contact the distal aperture of the shaft or wire. In a deployed configuration the proximal portion of the first wire directly contacts the distal aperture of the shaft or wire.

Example 6d

The system of example 5d, wherein: in the non-deployed configuration the distal portion of the third wire does not directly contact the proximal aperture of the shaft or wire. In the deployed configuration the distal portion of the third wire directly contacts the proximal aperture of the shaft or wire.

Example 7d

The system of example 6d, wherein the second wire has a proximal projection.

Example 8d

The system of example 2d, wherein the second wire has a proximal projection.

Example 9d

The system of example 8d, wherein: the second wire has a distal projection included in the second aperture. The second wire has a main body and the proximal and distal projections of the second wire both extend radially away from the main body of the second wire.

Example 10d

The system of example 9d, wherein: the distal projection of the second wire has proximal and distal walls. The second conduit includes a long axis. The proximal wall of the distal projection of the second wire is non-orthogonal to the long axis of the second conduit.

Example 11d

The system of example 2d comprising a third conduit. A portion of the third conduit is included within the first conduit but not the second conduit. Another portion of the third conduit is included within the second conduit but not the first conduit.

Example 12d

The system of example 11d, wherein the third conduit is fixedly coupled to at least one of the first or second conduits. The third conduit is slidably coupled to both of the first and second conduits.

Example 13d

The system of example 2d comprising a void between the medical implant and the first conduit. The second conduit includes a long axis; a first plane is orthogonal to the long axis. The first plane intersects the first conduit, the second aperture, the void, and the second wire.

Example 14d

The system of example 13d, wherein the first plane intersects the first wire.

Example 15d

The system of example 13d, wherein the first conduit is more radiopaque than the second conduit.

Example 16d

The system of example 15d, wherein the first conduit includes at least one of platinum, iridium, tungsten, or combinations thereof.

Example 17d

The system of example 1d, wherein the first wire directly contacts the second wire and applies a force to maintain the second wire within the second aperture.

Example 18d

The system of example 1d, wherein: in a non-deployed configuration the shaft or wire overlaps the first wire a first overlapping distance. In a deployed configuration the shaft or wire overlaps the first wire a second overlapping distance that is less the first overlapping distance. The second conduit includes a long axis and the first and second overlapping distances are both parallel to the long axis.

Example 1e

A system comprising: a medical implant including a channel, a first aperture, and a second aperture that is located in a sidewall of the medical implant; a first wire, a second wire, a third wire, and a shaft or wire that couples the first wire to the third wire; a coil that includes the first wire but not the second wire; a first conduit: (a) releasably coupled to the medical implant, and (b) including the first wire and the second wire but not the coil; a second conduit: (a) releasably coupled to the medical implant, and (b) including the first wire, the second wire, and the coil; wherein: the first wire is: (a) included within the channel, and (b) traverses the first aperture but not the second aperture; the second wire is: (a) included within the channel, and (b) traverses the first and second apertures.

Example 2e

The system of example 1e, wherein the shaft or wire includes a distal aperture that includes the first wire and a proximal aperture that includes the third wire.

Example 3e

The system of example 2e, wherein the distal aperture is slidably coupled to the first wire and the proximal aperture is slidably coupled to the third wire.

Example 4e

The system according to any of examples 2e-3e, wherein: a proximal portion of the first wire is proximal to the distal aperture and has an outer diameter that is larger than an inner diameter of the distal aperture; a distal portion of the third wire is distal to the proximal aperture and has an outer diameter that is larger than an inner diameter of the proximal aperture.

Example 5e

The system according to any of examples 2e-4e, wherein: in a non-deployed configuration the proximal portion of the first wire does not directly contact the distal aperture of the shaft or wire; in a deployed configuration the proximal portion of the first wire directly contacts the distal aperture of the shaft or wire.

Example 6e

The system of example 5e, wherein: in the non-deployed configuration the distal portion of the third wire does not directly contact the proximal aperture of the shaft or wire; in the deployed configuration the distal portion of the third wire directly contacts the proximal aperture of the shaft or wire.

Example 7e

The system according to any of examples 5e-6e, wherein: the second wire has a proximal projection that is proximal to at least a portion of the coil; in the non-deployed configuration the proximal projection does not directly contact the coil; in the deployed configuration the proximal projection directly contacts the coil.

Example 8e

The system according to any of examples 1e-7e, wherein the second wire has a proximal projection that is proximal to at least a portion of the coil.

Example 9e

The system of example 8e, wherein: the second wire has a distal projection included in the second aperture; the second wire has a main body and the proximal and distal projections of the second wire both extend radially away from the main body of the second wire.

Example 10e

The system according to any of examples 8e-9e, wherein: the distal projection of the second wire has proximal and distal walls; the second conduit includes a long axis; the proximal wall of the distal projection of the second wire is non-orthogonal to the long axis of the second conduit.

Example 11e

The system according to any of examples 1e-10e comprising a third conduit, wherein: a portion of the third conduit is included within the first conduit but not the second conduit; another portion of the third conduit is included within the second conduit but not the first conduit.

Example 12e

The system of example 11e, wherein: the third conduit is fixedly coupled to at least one of the first or second conduits; the third conduit is slidably coupled to both of the first and second conduits.

Example 13e

The system according to any of examples 1e-12e comprising a void between the medical implant and the first conduit, wherein: the second conduit includes a long axis; a first plane is orthogonal to the long axis; the first plane intersects the first conduit, the second aperture, the void, and the second wire.

Example 14e

The system of example 13e, wherein the first plane intersects the first wire.

Example 15e

The system according to any of examples 1e-14e, wherein the first conduit is more radiopaque than the second conduit.

Example 16e

The system of example 15e, wherein the first conduit includes at least one of platinum, iridium, tungsten, or combinations thereof.

Example 17e

The system according to any of examples 1e-16e, wherein the first wire directly contacts the second wire and applies a force to maintain the second wire within the second aperture.

Example 18e

The system according to any of examples 1e-17e, wherein the coil is non-releasably coupled to the distal actuation cord.

Example 19e

The system according to any of examples 1e-18e, wherein: in a non-deployed configuration the shaft or wire overlaps the first wire a first overlapping distance; in a deployed configuration the shaft or wire overlaps the first wire a second overlapping distance that is less the first overlapping distance; the second conduit includes a long axis and the first and second overlapping distances are both parallel to the long axis.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a side of a substrate is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first layer "on" a second layer is directly on and in immediate contact with the second layer unless such is specifically stated; there may be a third layer or other structure between the first layer and the second layer on the first layer. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A system comprising:
    an implant including a shape memory polymer (SMP) non-releasably coupled to a collar;
    a distal actuator wire, a retention wire, a proximal actuator wire, and a shaft that couples the distal actuator wire to the proximal actuator wire;
    a coil that includes the distal actuator wire but not the retention wire;
    a first conduit: (a) releasably coupled to the collar, and (b) including the distal actuator wire and the retention wire but not the coil;
    a second conduit: (a) releasably coupled to the collar, and (b) including the distal actuator wire, the retention wire, and the coil;
    wherein:
        the collar includes a channel, a first aperture, and a second aperture that is located in a sidewall of the collar;
        the distal actuator wire is: (a) included within the channel, and (b) traverses the first aperture but not the second aperture;
        the retention wire is: (a) included within the channel, and (b) traverses the first and second apertures.

2. The system of claim 1, wherein the shaft includes a distal aperture that includes the distal actuator wire and a proximal aperture that includes the proximal actuator wire.

3. The system of claim 2, wherein the distal aperture is slidably coupled to the distal actuator wire and the proximal aperture is slidably coupled to the proximal actuator wire.

4. The system of claim 3, wherein:
    a proximal portion of the distal actuator wire is proximal to the distal aperture and has an outer diameter that is larger than an inner diameter of the distal aperture;
    a distal portion of the proximal actuator wire is distal to the proximal aperture and has an outer diameter that is larger than an inner diameter of the proximal aperture.

5. The system of claim 4, wherein:
    in a non-deployed configuration the proximal portion of the distal actuator wire does not directly contact the distal aperture of the shaft;
    in a deployed configuration the proximal portion of the distal actuator wire directly contacts the distal aperture of the shaft.

6. The system of claim 5, wherein:
    in the non-deployed configuration the distal portion of the proximal actuator wire does not directly contact the proximal aperture of the shaft;
    in the deployed configuration the distal portion of the proximal actuator wire directly contacts the proximal aperture of the shaft.

7. The system of claim 6, wherein:
    the retention wire has a proximal projection that is proximal to at least a portion of the coil;
    in the non-deployed configuration the proximal projection does not directly contact the coil;
    in the deployed configuration the proximal projection directly contacts the coil.

8. The system of claim 2, wherein the retention wire has a proximal projection that is proximal to at least a portion of the coil.

9. The system of claim 8, wherein:
    the retention wire has a distal projection included in the second aperture;

the retention wire has a main body and the proximal and distal projections of the retention wire both extend radially away from the main body of the retention wire.

10. The system of claim 9, wherein:
the distal projection of the retention wire has proximal and distal walls;
the second conduit includes a long axis;
the proximal wall of the distal projection of the retention wire is non-orthogonal to the long axis of the second conduit.

11. The system of claim 2 comprising a third conduit, wherein:
a portion of the third conduit is included within the first conduit but not the second conduit;
another portion of the third conduit is included within the second conduit but not the first conduit.

12. The system of claim 11, wherein:
the third conduit is fixedly coupled to at least one of the first or second conduits;
the third conduit is slidably coupled to both of the first and second conduits.

13. The system of claim 2 comprising a void between the collar and the first conduit, wherein:
the second conduit includes a long axis;
a first plane is orthogonal to the long axis;
the first plane intersects the first conduit, the second aperture, the void, and the retention wire.

14. The system of claim 13, wherein the first plane intersects the distal actuator wire.

15. The system of claim 13, wherein the first conduit is more radiopaque than the second conduit.

16. The system of claim 15, wherein the first conduit includes at least one of platinum, iridium, tungsten, or combinations thereof.

17. The system of claim 1, wherein the distal actuator wire directly contacts the retention wire and applies a force to maintain the retention wire within the second aperture.

18. The system of claim 1, wherein the coil is non-releasably coupled to the distal actuator wire.

19. The system of claim 1, wherein:
in a non-deployed configuration the shaft overlaps the distal actuator wire a first overlapping distance;
in a deployed configuration the shaft overlaps the distal actuator wire a second overlapping distance that is less the first overlapping distance;
the second conduit includes a long axis and the first and second overlapping distances are both parallel to the long axis.

20. A system comprising:
a medical implant including a channel, a first aperture, and a second aperture that is located in a sidewall of the medical implant;
a first wire, a second wire, a third wire, and a shaft or wire that couples the first wire to the third wire;
a coil that includes the first wire but not the second wire;
a first conduit: (a) releasably coupled to the medical implant, and (b) including the first wire and the second wire but not the coil;
a second conduit: (a) releasably coupled to the medical implant, and (b) including the first wire, the second wire, and the coil;
wherein:
the first wire is: (a) included within the channel, and (b) traverses the first aperture but not the second aperture;
the second wire is: (a) included within the channel, and (b) traverses the first and second apertures.

21. The system of claim 20, wherein the shaft or wire includes a distal aperture that includes the first wire and a proximal aperture that includes the third wire.

22. The system of claim 21, wherein:
a proximal portion of the first wire is proximal to the distal aperture and has an outer diameter that is larger than an inner diameter of the distal aperture;
a distal portion of the third wire is distal to the proximal aperture and has an outer diameter that is larger than an inner diameter of the proximal aperture.

23. The system of claim 21, wherein:
in a non-deployed configuration the proximal portion of the first wire does not directly contact the distal aperture of the shaft or wire;
in a deployed configuration the proximal portion of the first wire directly contacts the distal aperture of the shaft or wire.

24. The system of claim 20 comprising a void between the medical implant and the first conduit, wherein:
the second conduit includes a long axis;
a first plane is orthogonal to the long axis;
the first plane intersects the first conduit, the second aperture, the void, and the second wire.

25. The system of claim 20, wherein the first wire directly contacts the second wire and applies a force to maintain the second wire within the second aperture.

* * * * *